United States Patent [19]
Glickman

[11] Patent Number: 5,897,533
[45] Date of Patent: Apr. 27, 1999

[54] CATHETER FLOW AND LATERAL MOVEMENT CONTROLLER

[75] Inventor: Morton G. Glickman, New Haven, Conn.

[73] Assignee: Delcath Systems, Inc., Stamford, Conn.

[21] Appl. No.: 08/922,236

[22] Filed: Sep. 2, 1997

[51] Int. Cl.⁶ ..................................................... A61M 5/00
[52] U.S. Cl. ............................. 604/256; 604/96; 604/236
[58] Field of Search .................................. 604/256, 236, 604/280, 283, 246–250, 183, 187, 49, 51, 53, 96–101

[56] References Cited

U.S. PATENT DOCUMENTS

| | | | |
|---|---|---|---|
| 5,069,662 | 12/1991 | Bodden | 604/101 X |
| 5,411,479 | 5/1995 | Bodden | 604/96 X |
| 5,489,274 | 2/1996 | Chu et al. | 604/248 |
| 5,597,377 | 1/1997 | Aldea | 604/93 |

Primary Examiner—John D. Yasko
Attorney, Agent, or Firm—Stephen E. Feldman, P.C.

[57] ABSTRACT

An arrangement for controlling the flow of blood between the annulus between a catheter and an elastomeric tube which encases it is provided. The arrangement also controls the ease of lateral movement of the catheter in relationship to the elastomeric tube. The arrangement includes a substantially rigid telescoping tube for supporting the elastomeric tube therewithin. The rigid telescoping tube further includes an inner tube having a pin disposed on the outer circumference thereof; and an outer tube having an opening therein forming a slot, and a plurality of substantially equally spaced stops; a first clamping arrangement for fixing one end of the elastomeric tube to the end of the outer tube furthest from the inner tube; and, a second clamping arrangement for fixing the other end of the elastomeric tube to the end of the inner tube furthest from the outer tube.

7 Claims, 3 Drawing Sheets

CATHETER FLOW AND LATERAL MOVEMENT CONTROLLER

BACKGROUND OF THE INVENTION

This invention relates to a method and apparatus for controlling the flow of a fluid through a conduit and the positioning of an element in a conduit. More particularly, the invention relates to a method and apparatus for controlling the flow of blood through a conduit and the positioning of a catheter in a catheter sheath. More particularly, this invention pertains to an elastic valve apparatus for preventing leakage of blood through an introducing catheter sheath inserted in a vessel and around a catheter inserted in the catheter sheath.

PRIOR ART

In the treatment of certain medical conditions, it is frequently necessary to repeatedly introduce a catheter for injection of fluids into blood vessels of a patient. It is common practice in order to minimize discomfort to the patient and to insure repeated access to the blood vessel in question, to install an "introducing sheath" in a more or less permanent fashion at an appropriate site on a patient. The sheaths are then used as the conduit through which a catheter can be introduced for injection of the desired medication or treatment materials into the blood vessel of the patient. Frequently, in treatment of cancers and other types of serious illnesses, repeated insertions of a catheter are required to introduce a variety of medications and this requires insertion and removal of a catheter repeatedly over time. While the catheter ferrule can be tightened about the introducing sheath ferrule to form a tight seal during the use of the catheter, when the catheter is being inserted and withdrawn and after the catheter is withdrawn, blood or other fluids can readily exit through the introducing sheath around the catheter and directly out after the catheter is removed. This causes an undesired leakage of blood or other fluid, both during and after insertion of the catheter.

Various methods have been suggested in the past for limiting this leakage with the most successful method known to applicant being the use of a latex diaphragm mounted in the introducing sleeve which has a small hole in the center and through which the catheter can be inserted. As the catheter is inserted, the diaphragm expands to accommodate the catheter and reduces the leakage of blood or other fluids about the catheter during use in the introducing sheath. When the catheter is withdrawn, the diaphragm closes to shut off the flow of fluids. While this has worked in certain instances, particularly where the catheter is of a very small diameter, for larger sized catheters and larger sized introducing sheaths, the latex diaphragm has tended to leak excessively. Also, in certain types of treatments, it has been found that a balloon catheter has been required and it has been found to be virtually impossible to insert a latex balloon catheter through a latex diaphragm, since the diaphragm tends to strip the latex balloon from the catheter. Accordingly, when a latex balloon catheter is to be used, the introducing sheath has generally had to be one without any leakage prevention means.

Medical techniques which require the use of balloon catheters have become increasingly important in the field of medicine.

For example, U.S. Pat. No. 5,411,479 to Bodden, teaches the perfusion of a high concentration of an agent to treat an organ, such as anti-cancer agents through a body organ containing a tumor, without their entering the body's general circulation, removing them from the organ with effluent blood and transporting the contaminated blood to an extracorporeal circuit where the blood is treated to remove the contamination, and returning the treated blood to the body. The process prevents toxic levels of the agents from entering the body's general circulation while delivering lethal doses of the agents to the tumor. There are described various apparatus for effecting the intra- and extracorporeal treatment of such contaminated blood.

U.S. Pat. 5,069,662 to Bodden, teaches the perfusion of a high concentration of an agent to treat an organ, such as anti-cancer agents through a body organ containing a tumor, without their entering the body's general circulation, removing them from the organ with effluent blood and transporting the contaminated blood to an extracorporeal circuit where the blood is treated to remove the contamination, and returning the treated blood to the body. The process prevents toxic levels of the agents from entering the body's general circulation while delivering lethal doses of the agents to the tumor. There are described various apparatus for effecting the intra- and extracorporeal treatment of such contaminated blood.

U.S. Pat. No. 5,597,377, to Aldea teaches a catheter for retroperfusion of myocardium has an infusion tip, such that when retroperfusing myocardium, the tip extends within the coronary sinus to a depth in a range of about 2 to 4 inches (5 to 10 cm) from the coronary sinus ostium. The catheter also comprises a tube defining at least three channels. The channels include an infusion channel, which has a first infusion end coupled to an infusion port located in the infusion tip and a second infusion end coupled to an outlet orifice of a pump; a withdrawal channel, which has a first withdrawal end coupled to a withdrawal port located in the superior vena cava and a second withdrawal end coupled to an inlet orifice of the pump; and a pressure monitoring channel for monitoring pressure at pressure port at the infusion tip having a first monitoring end coupled to the pressure port and a second monitoring end coupled to a pressure sensor. The catheter also has a microprocessor for controlling the pump and measuring a rate of retroperfusate flow, whereby autologous venous blood entering the withdrawal port is continuously discharged at the infusion port at a flow rate in a range of about 5 to 50 mil./min. and at a pressure less than about 15 mm Hg. The tube and tip are made from biocompatible, non-thrombogenic material. Further, the catheter has remotely identifiable markers spaced along the tube, and a marker is located at said infusion tip. The invention also is a method for coronary sinus retroperfusion. The method includes the steps of inserting the catheter through the patient's jugular vein; guiding the catheter's infusion tip into the coronary sinus, such that when retroperfusing myocardium, the tip extends within the coronary sinus to a depth in a range of about 2 to 4 inches (5 to 10 cm) from the coronary sinus ostium; and providing a non-synchronized retroperfusate flow of autologous venous blood at a rate in a range of about 5 to 50 mil./min. and at a pressure less than about 15 mm Hg.

U.S. Pat. No. 5,569,182 Twardowski, et. al., teaches blood which is circulated through a multiple lumen catheter which connects between a vein of a patient and the blood treatment device. The catheter and the lumens thereof each define distal ends which are positioned within the vein. By this invention, one withdraws blood from the vein through one of the lumens at a flow rate of at least about 200 ml./min. while also inserting blood into the vein through another of said lumens at a similar flow rate. The distal ends of the lumens are longitudinally spaced from each other by no more than about 5 mm. It have been found that the following advantages can be achieved by this method: less clot formation coupled with low direct blood recirculation and longer catheter survival. Also, the catheter works well in either direction of blood flow through the respective lumens.

U.S. Pat. No. 5,509,897, to Twardowski, et. al., teaches a catheter for hemodialysis comprises a flexible catheter tube defining a plurality of separate lumens. The catheter defines an arc angle of generally U-shape in its natural, unstressed configuration. Thus, the catheter may be implanted with a distal catheter portion residing in a vein of the patient, the distal catheter portion being of substantially the shape of the vein in its natural, unstressed condition. Also, a proximal catheter portion resides in a surgically created tunnel extending from the vein and through the skin of the patient, this section of the Catheter also being typically in its natural, unstressed condition. Thus blood may be removed from the vein through one lumen of the catheter, and blood may be returned to the vein through another lumen of the catheter, while the catheter is subject to long term indwelling in the body. Improved results are achieved because of the lack of mechanical stress in the shape of the catheter, which stress causes the catheter to press unduly against adjacent tissues.

U.S. Pat. No. 5,505,698, to Booth, et. al., teaches a catheter for supplying liquid to the coronary sinus in a perfusion procedure comprising a tubular catheter body having an interior lumen, a proximal end, and a distal end; and an inflatable cuff (balloon) adjacent the distal end of the catheter. The cuff has a proximal end and a distal end, each of which encircle the catheter body and hermetically seal thereto. The cuff further comprises an elongated central section having a length of at least 1 inch. When the inflated cuff is positioned a sufficient distance into the coronary sinus to firmly retain the cuff therein, it blocks the left coronary vein where it meets the coronary sinus. Further, the cuff can comprise end panels defined between the central section and the proximal and distal cuff ends. The end panels have a shape which allows for flexure between the central section and the cuffs proximal and distal ends.

U.S. Pat. No. 5,489,274, to Chu, et. al., teaches an easy operating, durable closure device for controlling the closure of a passageway in for example valves and the like used in medical applications. The device includes a cam surface arranged about the circumference of a resilient tubing member. Rotation of the cam controls the radial position of a compression member that compresses the tubing member to effect closure. Such a closure device, or a two-part rotary closure device in general, is constructed to receive an accessory component such as a syringe, the rotary connecting movement of which automatically opens the closure device. The device may be used as a torqugeable handle for a guidewire gripped in the passage. A large scale version of the device is joined to an introducer sheath, sized to pass an introducer catheter for e.g., a Green field filter, or to close upon a guidewire to prevent backflow of blood.

U.S. Pat. No. 5,462,529, to Simpson, et. al., teaches a catheter device for treatment of disease in biological conduits. The device has inner and outer coaxial catheter members, each having an inflatable balloon attached near its distal end. When the balloons are inflated, a sealed treatment chamber is created between the balloons. The length of the treatment chamber is adjustable by sliding the coaxial catheter members with respect to each other to obtain a desired separation between the attached balloons before inflation. Biological debris is trapped within the chamber and removed by infusion and aspiration of a flushing fluid, reducing the risk of myocardial infarction. Adjunctive treatment devices can be inserted into the sealed treatment chamber through a lumen of the outer coaxial member.

U.S. Pat. No. 5,458,583, to McNeely, et. al. A system and method for inserting a gastrostomy catheter through a passageway formed through the abdominal and stomach walls of a patient. The gastrostomy catheter is mounted onto a dilatation catheter with a dilatation member such as an inelastic balloon on the distal extremity thereof. An introducer needle is first advanced through the walls of the patient's abdomen and stomach into the interior of the stomach and then a guidewire is advanced through the inner lumen of the needle into the stomach interior. The gastrostomy catheter-dilatation catheter assembly is advanced over the guidewire until the balloon on the dilatation catheter is in proper position crossing both the abdominal and gastric walls. Upon inflation of the balloon on the dilatation catheter, the passageway is expanded enough so that the gastrostomy catheter can be advanced therethrough to dispose the distal end of the gastrostomy catheter within the interior of the stomach. The balloon on the distal end of the gastrostomy catheter is inflated so as to form an internal retention member and the catheter withdrawn in order to urge the inflated balloon against the stomach wall. Preferably, the gastrostomy catheter has an external retention ring on the shaft thereof which is slid against the exterior of the patient's abdomen to seal the passageway through the abdominal wall.

U.S. Pat. No. 5,423,745 to Todd, et. al., teaches balloon catheters for use in infusing a solution into a body passageway, and their methods of use and manufacture. Each catheter contains at least one lumen through which a solution flows into the body. The balloons of each catheter are secured to the proximal end of the catheter, and each have a plurality of protuberances projecting outwardly from the outer surface of the balloons for the purpose of firmly gripping the walls of the body passageway so as to secure placement of the catheter within the passageway. A malleable wire assists in retaining the catheter in position within the body passageway. A double balloon catheter allows sealing of the body passageway to be accomplished separately from securely gripping the walls.

U.S. Pat. No. 5,405,320, to Twardowski, et. al., teaches a catheter for hemodialysis comprises a flexible catheter tube deferring a plurality of separate lumens. The catheter defines an arc angle of generally U-shape in its natural, unstressed configuration. Thus, the catheter may be implanted with a distal catheter portion residing in a vein of the patient, the distal catheter portion being of substantially the shape of the vein in its natural, unstressed condition. Also, a proximal catheter portion resides in a surgically created tunnel extending from the vein and through the skin of the patient, this section of the catheter also being typically in its natural, unstressed condition. Thus blood may be removed from the vein through one lumen of the catheter, and blood may be returned to the vein through another lumen of the catheter, while the catheter is subject to long term indwelling in the body. Improved results are achieved because of the lack of mechanical stress in the shape of the catheter, which stress causes the catheter to press unduly against adjacent tissues.

U.S. Pat. No. 5,398,687, to Abell, teaches new devices and methods for detecting and diagnosing motility abnormalities within the pancreaticobiliary tree. In the first device, a modified ERCP catheter with electrical activity sensing is positionable within the biliary tract, and operates to sense electrical activity during the ERCP procedure. Electrical activity is sensed by two circumferential leads formed by bands of silver, located near the distal tip of the catheter. The detection of electrical activity, in combination with the simultaneous radioscopic visualization of the biliary tract, provides a detailed motility profile for the physician without requiring the additional use of a perfusion catheter. A second device is also disclosed which detects motility within the biliary tract by the simultaneous sensing of electrical activity and surrounding fluid pressure. A biliary catheter has two circumferential silver leads and three perfusion lumens whose outlets are alternately spaced between the silver leads. When positioned within the biliary tract, this catheter yields valuable data correlating electrical activity and the corresponding occurrence of muscle activity. By the sequential detection of pressure changes at the proximal, medial, and distal perfusion outlets interspersed between the electrical activity leads, both the presence and direction of muscle activity are sensed in relation to the sensed electrical activity about the leads.

U.S. Pat. No. 5,397,310, to Chu, et. al., a catheter introducer sheath assembly, for introduction into a body passage of a catheter containing a filter comprises a flexible introducer sheath joined to the distal end of a closure device forming a through-passage with a diameter sufficient to pass the catheter therethrough. The closure device has a resilient member in the through-passage and two rotatable body portions, one stationary with respect to the resilient member, and the other rotatable about the axis of the resilient member with an internal cam circumferentially spaced around the axis. A compression member positioned radially in an extending aperture makes contact with both the resilient member and the cam surface to vary the through-passage allowing the operator to manually control the passage of the device. The sheath assembly receives a cathetory guidewire that slides through and extends beyond the closure device and the sheath. In another aspect, the combination sheath assembly and closure device forms a catheter introducer kit constructed to receive a stabilizer and a catheter of sufficiently large diameter to house a vena cava filter, and to pass the filter through the closure device and sheath for placement in the body by means of a dilator attached to the end of the sheath to facilitate guiding the filter to the desired position for its release from the sheath. The closure device is adjustable to prevent any backflow of fluid such as blood from the assembly during the filter placement procedure.

U.S. Pat. No. 5,397,307, to Goodin, teaches an intravascular material delivery dilation catheter having a pair of longitudinally spaced inflatable balloons with a drug delivery region defined therebetween. The catheter is ideally suited for use after a PTCA procedure, wherein the proximate balloon seals the blood vessel while the distal balloon is uniquely contoured when inflated to define fluid communication paths therepast and proximate a blood vessel to be treated. The distal balloon, when inflated, has four lobes but could also be textured. Each lobe is separated from the next by a groove, which groove in combination with the blood vessel inner wall forms a fluid communication path therebetween. Upon inflation of both balloons in a blood vessel, a medicament such as heparin can be injected, via the drug delivery region between the inflated balloons, wherein the medicament flows past the distal balloon at a selected rate. Accordingly, a medicament can be injected directly to a treatment site rather than injected as a bolus dose, thus, a smaller dosage may be employed to minimize side effects. Alternatively, perfusion can be accomplished by only partially inflating the proximate balloon to constrict flow therepast, or eliminating the proximate balloon entirely, where the drug delivery region is disposed upstream of the contoured distal balloon.

U.S. Pat. No. 5,370,614, to Amundson, et. al., teaches a balloon catheter includes a sheath surrounding the balloon, the sheath having a longitudinal line of weakness and a drug-containing viscous matrix material intermediate between the balloon and the sheath such that when the balloon is positioned and inflated in the body lumen it causes the sheath to burst at the line of weakness and release viscous matrix material onto said body lumen. The device provides accurate placement of the dosage required at the location in need of treatment. The catheter is especially useful in balloon angioplasty procedures.

U.S. Pat. No. 5,338,301, to Diaz, teaches an extendable balloon-on-a-wire catheter which includes a telescoping exchange core wire mounted along the inside lumen of the longitudinal tube of the balloon-on-a-wire assembly. In the preferred embodiment, the exchange core wire is mounted within a hypodermic tube secured to the core wire of the balloon-on-a-wire assembly. A multiple component system includes this balloon-on-a-wire assembly together with an over-the-wire catheter which slidably passes over the elongated body of the balloon-on-a-wire assembly. Preferably, the relative sizing of these components of the system is such that the over-the-wire catheter does not pass over the balloon of the balloon-on-a-wire assembly. In a treatment procedure, the balloon-on-a-wire assembly achieves dilation of a lesion or a stenosis, after which it is moved somewhat distally to clear the stenosis. When the over-the-wire catheter is used, it is slidably moved over the balloon-on-a-wire assembly until its treatment location reaches the stenosis. During the procedure, the exchange core wire can be telescopically extended to a length such that the surgeon can readily grasp the balloon-on-a-wire assembly or its exchange core wire during manipulation of the over-the-wire catheter.

U.S. Pat. No. 5,324,261, to Amundson, et. al., teaches a balloon catheter includes a sheath surrounding the balloon, the sheath having a longitudinal line of weakness and a drug-containing viscous matrix material intermediate between the balloon and the sheath such that when the balloon is positioned and inflated in the body lumen it causes the sheath to burst at the line of weakness and release viscous matrix material onto said body lumen. The device provides accurate placement of the dosage required at the location in need of treatment. The catheter is especially useful in balloon angioplasty procedures U.S. Pat. No. 5,304,121, to Sahatjian, teaches a catheter and methods for delivering drug to tissue at a desired location of the wall of a body lumen. The catheter is constructed for insertion in a body lumen and has a catheter shaft and an expandable portion mounted on the catheter shaft. The expandable portion is expandable to a controlled pressure to fill the cross-section of the body lumen and press against the wall of the body lumen. In one embodiment, at least a portion of the exterior surface of the expandable portion is defined by a coating of a tenaciously adhered swellable hydrogel polymer. Incorporated in the hydrogel polymer is an aqueous solution of a preselected drug to be delivered to the tissue or plaque. The hydrogel polymer and drug are selected to allow rapid release of a desired dosage of the drug from the hydrogel polymer coating during compression of the hydrogel polymer coating against the wall of the lumen when the expandable portion is expanded. In other embodiments the polymer is released from the expandable portion in response to pressure, to coat the wall of the body lumen.

U.S. Pat. No. 5,286,259, to Ganguly, et. al., teaches a catheter (10) having a stepped coaxial construction formed by and internal tube 12) and an external tube (14). The internal tube includes a distal pressure lumen (26), a balloon inflation lumen (28), and a sensor lumen (30). The external tube includes the first proximal pressure lumen (48), second proximal pressure lumen (50), injection lumen (52), and transducer lead lumen (54). A cylindrical transducer (16), sensor (18), and balloon (42) are supported on the internal and external tubes, which allow the transducer to be coaxially mounted thereon. The catheter has a high lumen count, large lumen cross-sectional area, is easy to construct and use, and allows cardiac output to be measured continuously without sacrificing other currently available catheter functions.

U.S. Pat. No. 5,281,200, to Corso, Jr., et. al., teaches a balloon catheter system which includes a balloon-on-a-wire assembly and an over-the-wire catheter which slidably passes over the elongated body of the balloon-on-a-wire assembly, but not over its balloon. In the procedure by which the system is used, the balloon-on-a-wire assembly achieves an initial dilation or predilation of a lesion or stenosis, after which it is moved somewhat distally to clear the predilated stenosis. The over-the-wire catheter then is slidably moved over the balloon-on-a-wire assembly until its balloon reaches and dilates the predilated stenosis. After dilation is completed, the system is removed from the body vessel thus treated.

U.S. Pat. No. 5,279,546, to Mische, et. al., teaches an apparatus and method for dissolving and removing material which tends to occlude a body passage way, such as an artery. The device employs a dual catheter system arranged in coaxial fashion. Each of the catheters has an inflatable balloon at its distal tip. Inflating the two balloons occludes the body passage way both proximal and distal to the treatment area, thus isolating it from fluid contact with the rest of the body. Because concentric catheters are used, the distance between the balloons and hence the size of the treatment area is adjustable. The thrombolytic agent is infused through orifices in the inner catheter in the region between the two balloons. A piezo electric device supplies ultrasonic agitation within the treatment area. A pressure device monitors the body passage way for unsafe conditions. Aspiration is accomplished through one or more lumens in the outer catheter. Ultrasonic agitation may be employed with the aspiration also to break up masses of material which may be too big to pass through the exit lumen cross section.

U.S. Pat. No. 5,254,089, to Wang, teaches an inflatable medical device for the delivery of medications to an organ in the body including a catheter having a plurality of lumens disposed therein. The distal end of the catheter is adapted to be disposed within a bodily organ. A hollow, inflatable, medication-deliverable balloon is disposed on the distal end of the catheter and the interior of the balloon is in fluid flow relationship with one of the lumens to enable the balloon to be inflated. An array of conduits is disposed within the walls of the balloon for the delivery of medications to predetermined locations within said bodily organ. Another lumen in the catheter shaft is provided to deliver medications to the conduits in the wall of the balloon and an egress for the medications so that they may be dispensed at the site being treated.

U.S. Pat. No. 5,236,417, to Wallis, teaches a cholangiography catheter for injecting dye into a cystic duct during laparoscopic cholangiography. The catheter includes a bifurcated connector having a length of tubing and a check valve mounted to each arm of the connector. A saline syringe is coupled to one check valve and a dye syringe is coupled to the other check valve. The check valves and respective syringes are color coordinated to preclude inadvertently using the wrong syringe. The catheter is fabricated from a medical grade polymer having a preselected degree of compliant memory and includes indicia for providing a visual indication of the depth of penetration of the tip of the catheter into the cystic duct.

U.S. Pat. No. 5,226,427, to Buckberg, et. al., teaches a stylet for use with a retrograde cardioplegia catheter and its methods of use. The stylet includes a stylet rod, a handle on the proximal end of the stylet rod and a predetermined curve in the distal end of the stylet rod. The handle has a thumb rest on the proximal end and a one or two finger loops extending outward from the handle. An obturator is located on the distal end of the predetermined curve to impede blood flow through a tip of the cardioplegia catheter during insertion of the catheter. The invention also contemplates methods for using the stylet.

U.S. Pat. No. 5,209,723, to Twardowski, et. al., teaches a multiple lumen, intravenous catheter for hemodialysis or the like defines a distal end portion in which at least a pair of the catheter lumens each communicates with the exterior through aperture means. By this invention the aperture means of one of the lumens defines a first port at essentially the distal catheter end, and the aperture means of the other of the lumens defines a second port spaced proximally along the catheter from the distal end and first port. The second port is positioned to face radially inwardly to at least a slight degree to avoid engagement of the wall of the blood vessel that the catheter occupies. Additionally, the tip of the catheter distal of the second port is preferably of substantially helically shape, being sized to assist in keeping the second port away from the blood vessel wall. As another feature, the catheter may be angled in its as-manufactured, unstressed condition to avoid pressing by elastic memory against internal blood vessel walls. Also, the catheter may define an inflatable balloon positioned between the first and second ports as a means for spacing particularly the second port away from blood vessel walls.

U.S. Pat. No. 5,209,717, to Schmoll, et. al., teaches a method and a device for the application and the removal of locally applied active substances against solid tumors, which device consists of a catheter (1) to be positioned distally to the tumor for the collection of blood coming from the tumor, a pump (2) and a catheter (3) connected thereto and returning the blood into the body. The device is characterized in that between the two catheters (1, 3) there is present at least one container (4) capable of allowing blood to pass therethrough and containing immobilized substances having high affinity against the applied active substance.

U.S. Pat. No. 5,209,239, to Watanabe, et. al., teaches an apparatus for cystographic inspection used for observing and measuring the urethrophaxis portion and posterourethovesical angle of a patient of the acraturesis caused by a ventral pressure. The apparatus comprises a catheter, in the housing of which a flexible urethral locus indicating member, provided with a marking member, is positioned. The flexed condition of the urethral and the posterourethrovesical angle can be clearly confirmed by the urethral locus indicating member, and the position of an exterior urethral opening member, and position of an exterior urethral opening can be surely grasped by the marking member which can be roentgenographed and which is positioned on the urethral locus indicating member and that it is prevented from penetrating into the uretra and this assists in examining of the external urethral opening during roentgenography of the urethral locus indicating member of the catheter.

U.S. Pat. No. 5,167,623, to Cianci, et. al., teaches a multilumen catheter having a distal portion with a soft tip and reduced cross-section. The multilumen catheter of the present invention includes a flexible, elongated first catheter tube and a flexible, elongated, dual-lumen catheter tube which has a first and second lumens integrally formed and is disposed within the first catheter tube. The cross-section of the dual-lumen catheter tube is smaller than that of the first catheter tube and therefore, an independent, single lumen is defined in the space between the first catheter tube and the dual-lumen catheter tube. The dual-lumen catheter tube extends beyond the distal end of the first catheter tube thereby providing an overall reduced cross-section of the distal portion of the present multilumen catheter. Furthermore, the dual-lumen catheter tube may be formed from a softer material than that of the first catheter tube thereby providing a softer distal portion of the present multilumen catheter. A protective hub encapsulates and secures the proximal ends of the first and dual-lumen catheter tubes, and facilitates fluid communication between each of the lumens and fluid transfer devices.

U.S. Pat. No. 5,167,622, to Muto, a suction catheter provided with three conduits to provide the functions of suctioning, lavaging and oxygenating. The suction conduit is connected to a suction control member. The second conduit for the irrigating fluid is connected to a source of said fluid. The third conduit is connected to a source of gas under pressure. The gas conduit terminates within the irrigation conduit to form a common chamber at the distal end of the irrigation conduit from which fluid is propelled out by the pressurized gas. The gas may preferably contain oxygen.

U.S. Pat. No. 5,158,540, to Wijay, et. al., teaches a low-profile angioplasty catheter which is insertable through a guiding catheter. The angioplasty catheter has two balloons. The distal balloon dilates the stenosis. The proximal balloon is separately inflatable and selectively closes the annular passage between the angioplasty catheter and the guiding catheter. The angioplasty catheter has a central lumen with a series of openings allowing fluid communication from the central lumen into the annular passage proximally of the balloon which seals the annular passage. While the first balloon is inflated to dilate the stenosis, blood can be withdrawn from an arterial source through a lumen (or plurality thereof) in the guiding catheter and pumped into the annular passage between the angioplasty catheter and the guiding catheter. The blood then passes through the openings proximal to the proximal balloon into the central lumen of the PTCA catheter and flows beyond the distal tip of the angioplasty catheter to maintain circulation of the patient's blood at a point distal of the stenosis.

U.S. Pat. No. 5,122,115, to Marks, teaches a multiple lumen catheter specifically adapted for selective visualization of one or the other of the coronary arteries. One lumen of the multiple lumen catheter is adapted to deliver contrast agent to the coronary artery to be visualized while a second, and optionally a third, lumen is adapted to limit flow of contrast agent to one or more other locations in the aortic root complex. The invention also includes a method of preparing for coronary angiography using such a catheter.

U.S. Pat. No. 5,120,323, to Shockey, et. al., teaches a guide catheter system for use in the treatment of coronary artery disease includes a first single-lumen catheter of a relatively large internal diameter to pass a second guide catheter therethrough. The first guide catheter comprises an elongated flexible tube having a stainless steel braid embedded in the wall thereof for imparting desired torqueability characteristics to it. The first guide catheter is intended to be inserted at an appropriate point in the vascular system and then advanced until its distal end reaches the coronary ostium. The second guide catheter is fabricated by extruding a plastic, such as polyurethane thermoplastic resin over a tubular Teflon RTM core and because it is to be used within the lumen of the first catheter, it need not include a braided structure within its walls to prevent it from kinking. This allows the second catheter to be sufficiently slim to permit it to be advanced into a coronary artery while allowing fluids to be perfused between the outer wall of the second guide and the inner wall of the first guide catheter while still providing a sufficiently large inner lumen to pass a working catheter, e.g., an angioplasty or atherectomy catheter. An atraumatic tip is attached to the distal end of the second guide catheter.

U.S. Pat. No. 5,106,363, to Nobuyoshi, a dilation catheter defining a lumen and including a dilating member at the leading end, and a sheath defining a bore through which the dilation catheter is inserted to define a blood intake gap between the outer surface of the dilation catheter and the sheath bore and including a transverse bore branched from the sheath bore, a tube is connected at one end to the transverse bore and at another end to the lumen of the dilation catheter at a trailing end. When the sheath having the dilation catheter inserted therein is set in a blood vessel, a pump in the tube operates to take blood into the blood intake gap in the sheath, pass through the tube and the dilation catheter lumen, and feed back to the periphery of a lesion through the open leading end of the dilation catheter. The patient's own fresh blood can be injected without the need for a further cutdown or puncture for blood intake.

U.S. Pat. No. 5,102,390, to Crittenden, et. al., teaches a balloon angioplasty system includes a balloon dilatation catheter having an inflation and deflation lumen for the balloon and a main lumen extending the fall length of the catheter to provide fluid communication from the proximal to the distal end of the catheter. A microdilatation probe has a small diameter and can be passed through the main lumen of the dilatation catheter. The microdilatation probe has a balloon at its distal end which is collapsible to enable it to be passed through the main lumen of the dilatation catheter so that it can be projected distally beyond the distal tip of the dilatation catheter. The probe balloon is inflatable to a diameter no smaller than the diameter of the uninflated dilatation catheter. The probe and dilatation catheter are constructed so that fluid communication is maintained through the main lumen of the dilatation catheter while the microdilatation probe extends through the catheter thereby enabling liquids to be infused and pressure measurements to be taken while the probe is in place. The probe may include a distal tip which can hold a preset curve. In use, a stenosis which cannot be crossed by the dilatation catheter may be enlarged sufficiently to permit passage of the dilatation catheter by first projecting the dilatation probe into the stenosis, then inflating the probe balloon to enlarge the lumen of the stenosis sufficiently to thereafter receive the dilatation catheter.

U.S. Pat. No. 5,084,031, to Todd, et. al., teaches a three-way double stopcock and associated tubing with which to connect both a cardioplegia solution source and a pressure monitor for the solution selectively and alternatively to either an antegrade cardioplegia catheter or a retrograde cardioplegia catheter. The stopcock includes a hollow valve body with three solution infusion ports communicating to the interior thereof in a coplanar arrangement at a first longitudinal point on the valve body. Three cardioplegia pressure monitoring ports also communicate through the valve body to the interior thereof at a second longitudinal position distinct from the first. Mounted in the valve body is a cylindrical valve core selectively rotatable about the longitudinal axis thereof between a first position in which the cardioplegia solution source and the pressure monitor are coupled to the antegrade cannula and a second position in which the cardioplegia solution source and the pressure monitor are coupled to the retrograde catheter. Formed in the valve core are a set of valving passageways for communicating with selective of the infusion ports and a set of valving passageways for communicating with selective of the pressure monitoring ports.

U.S. Pat. No. 5,021,045, to Buckberg, et. al., teaches a retrograde cardioplegia catheter and its method of use. The catheter contains two lumens, an infusion lumen through which the cardioplegic solution flows and a pressure sensing lumen for monitoring the fluid pressure at the point where the solution exits the catheter. A slightly tapered, self-filling balloon is secured to the distal end of the catheter. Also, located at the distal end of the catheter is a soft, rounded tip to prevent damage to the sensitive intimal tissues of the coronary sinus. A stylet having a predetermined curve at the distal end and a handle at the proximal end is removably located within the infusion lumen. The predetermined curve at one end of the stylet enables the cardioplegia catheter to be inserted quickly and accurately within the coronary sinus through a very small incision made in the right atrium. After the catheter is securerd in place, the stylet is withdrawn. The catheter remains in position for the duration of the operation in order to periodically readminister the cardioplegia solution.

U.S. Pat. No. 5,004,455, to Greenwood, et. al., teaches a balloon catheter which comprises a balloon catheter body, a balloon, a main passage and an auxiliary passage. The balloon is provided on the periphery of the tip portion of the catheter body to inflate for blocking a bloodstream at a desired site inside blood vessels. The auxiliary passage is provided for inflating the balloon. The main passage is provided behind the balloon, having an opening to eject a drug. The tip portion of the balloon catheter is inserted into one of branches of the blood vessel near targeted affected part. A fluid is injected into the balloon so that the balloon blocks a bloodstream in the branches. Therefore, a drug is ejected through the main passage of the balloon catheter into other branches.

U.S. Pat. No. 4,883,459, to Calderon, teaches the study of tumors in the body of a patient in situ by a monitor, such as computer assisted tomography, X-ray or the like, while optimal flow paths through the tumor area are established. A catheter with a suction lumen and an infusion lumen, with seals associated with each, is placed in the patient's vein near the tumor. Flow is then sealed in the vein with the infusion seal. A carrier medium dye is injected into the tumor at selected flow rates and differential pressures. Flow of the dye through the tumor is observed on the monitor to determine optimal retrograde perfusion paths through the tumor for the selected flow rates and differential pressures. Once the optimal perfusion paths are noted, a preferential attack area in the tumor is located using a different, less dense carrier dye and increased fluid back pressure in the infusion system. Once the attack area in the tumor is located, microspheres with active ingredients, such as chemotherapy, can be selectively perfused through one of the paths in the tumor to the attack site and forced into the tumor, once at the attack site, using increased back pressure. The process may be cyclically repeated using the same or different active ingredients. The procedure may be repeated through the tumor in different paths and attack points at desired active ingredient dosages using increased back pressures.

U.S. Pat. No. 4,867,742, to Calderon, teaches the study of tumors in the body of a patient in situ by a monitor, such as computer assisted tomography, X-ray or the like, while optimal flow paths through the tumor area are established. A catheter with a suction lumen and an infusion lumen, with seals associated with each, is placed in the patient's vein near the tumor. Flow is then sealed in the vein with the infusion seal. A carrier medium dye is injected into the tumor at selected flow rates and differential pressures. Flow of the dye through the tumor is observed on the monitor to determine optimal retrograde perfusion paths through the tumor for the selected flow rates and differential pressures. Once the optimal perfusion paths are noted, microspheres with active ingredients, such as chemotherapy, can be selectively perfused through each of the paths in the tumor at desired flow rates, pressures and active ingredient dosages. Alternatively, microspheres with different active ingredients can be selectively introduced through the tumor in different paths at desired active ingredient dosages and established flow rates and pressures.

U.S. Pat. No. 4,820,261, to Schmoll, et. al., a device for the removal of active substances locally applied against solid tumors consists of a catheter (1) to be positioned distally to the tumor for the collection of blood coming from the tumor, a pump (2) and a catheter (3) connected thereto and returning the blood into the body. The device is characterized in that between the two catheters (1, 3) there is present at least one container (4) capable of allowing blood to pass therethrough and containing immobilized antibodies against the applied active substance.

U.S. Pat. No. 4,714,460, to Calderon, teaches catheter feedback methods and systems for optimizing the infusion of a drug, such as a chemotherapeutic agent via retrograde perfusion through the venous side of the vascular network to a selectively determined portion of a solid tumor. Monitoring and regulatory capability are provided for controlling the outflow of the drug and thereby for controlling the dose rate, the duration of exposure of the drug, the leakage factor, and the level of systemic toxicity, all critical factors in the successful treatment of solid tumors. A feedback loop for practicing the method comprises two concentric balloon catheters capable of extensive maneuvering and selective placement within the venous drainage of the vascular system, creating a third in-vivo space for repeated perfusion of the selected portion of a diseased organ as often as desired, providing maximum exposure of the chemotherapy to the tumor with minimum exposure to any other portions of the patient's body.

OBJECTS AND SUMMARY OF THE INVENTION

It is therefore an object of the present invention to provide a method and apparatus for overcoming the limitations of the prior art. It is another object of the present invention to provide a method and apparatus for sealing around a catheter inserted in an introducing sheath. It is a further object of the present invention to provide a method and apparatus for sealing around a catheter inserted into an introducing sheath and to shut off the flow of fluid through the sheath after removal of the catheter. It is yet another object of the present invention to provide an elastic valve for closing off the flow of fluids through a conduit.

It is yet a further object of the present invention to provide an elastic valve which may be repeatedly closed and opened to control flow of a fluid through a tube.

It is a still further object of the present invention to provide an elastic valve for shutting off a conduit that can be securely closed about an object in the fluid flow path in the conduit.

It has also been found to be very desirable in various medical procedures to be able to temporarily shut off the flow of blood or other fluids without damaging the blood vessel, the introducing sheath, the catheter, or without having to install a cap or other seal.

In a preferred embodiment of the present invention, this is accomplished by providing a valve having a generally cylindrical rigid, two-part, telescoping, outer shell and an inner flexible elastic tubular lining forming an inner shell sealed together at their ends to form a fluid-tight chamber therebetween. The outer shell can be telescoped in one of a plurality of different lengths by simply engaging a pin fixed to the inner of the parts to one of a plurality of stops on the outer of the parts. With this embodiment, if a catheter is in place in the tube, the valve will shut off leakage or fluid flow through the tube by sealing about the catheter and the catheter can be fixed in relationship to the sheath, to a degree proportional to the selected length of the outer shell.

BRIEF DESCRIPTION OF THE DRAWING

Further objects of the invention, together with additional features and advantages accruing therefrom will be apparent from the following description of a preferred embodiment shown in the accompanying drawings in which.

DETAILED DESCRIPTION OF THE DRAWINGS

THE PRIOR ART

Figure 1:
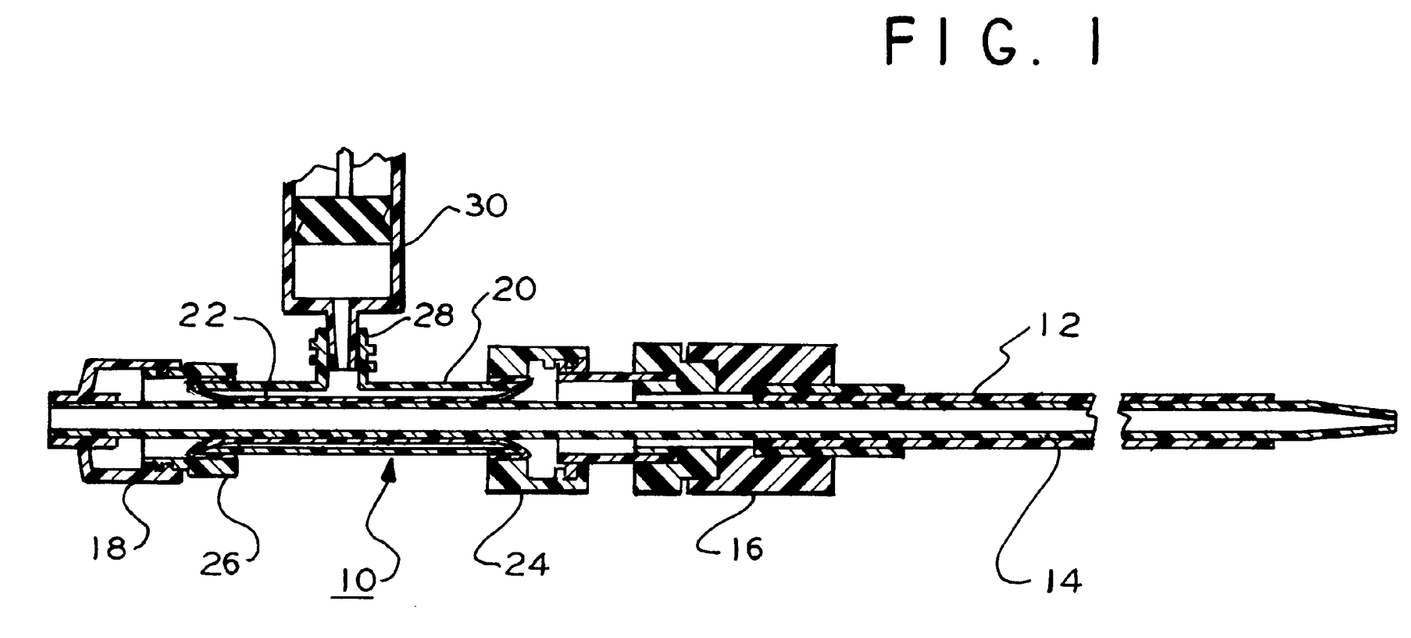
FIG. 1 is a cross sectional view of a valve in accordance with a prior art invention attached to an introducing sheath and catheter.

Referring now to FIG. 1 which exemplifies the prior art, there is shown a valve 10 installed on an introducing sheath 12 through which a catheter 14 has been inserted, as might be used in a patient for introducing a treatment or medication. The introducing sheath 12 is usually a plastic tube long enough to be semi-permanently placed in a patient's blood vessel, as is well known in the art. The usual ferrule 16 is provided at the proximal end for reception of catheter ferrules, closure ferrules, and other well-known devices used with a semi-permanently installed introducing sheath. The catheter 14 has a ferrule 18 which engages with the ferrule 16 on the introducing sheath with one ferrule being male, and the other ferrule being female. As shown in FIG. 1, the valve 10 of the present invention has a corresponding female 24 and male 26 connector at the ends thereof for installation in series in this sequence.

In the prior art predating the foregoing prior art arrangement, the catheter 14 would be introduced into the sheath 12 and the ferrule 18 locked about the ferrule 16. In this position, leakage of blood or other fluids around the catheter and out through the ferrules would be prevented as long as the two ferrules were locked together in sealing relationship. On removal of the catheter 14, a cap or other closure would have to be applied to the ferrule 16 to prevent leakage of fluids through the sheath 12. Also, during installation of the catheter, which can take some time, and during the removal of the catheter, there can be, and frequently is, significant leakage around the catheter through the sheath.

In the prior art predating the foregoing prior art invention, the ferrule 16 has sometimes been provided with a latex diaphragm at one end which has been essentially a layer of latex rubber having a small hole in the center which is adapted to expand and contract as a catheter 14 is inserted into and withdrawn from the diaphragm. As explained above, this has worked for smaller sizes somewhat, but has always left some leakage, and for larger sizes, has not been particularly satisfactory. Also, the diaphragm prevents usage of a catheter with a balloon on the end, as is frequently used in treatment of certain types of medical conditions.

Accordingly, the foregoing prior art invention provides the valve 10 which was installed on the end of the introducing sheath 12 and which acts as a shut off for blood or other fluids leaking from the sheath, and yet permits easy introduction of a catheter 14 into the sheath while simultaneously providing a sealing function around the catheter as it is installed, used and as it is withdrawn.

Figure 2:
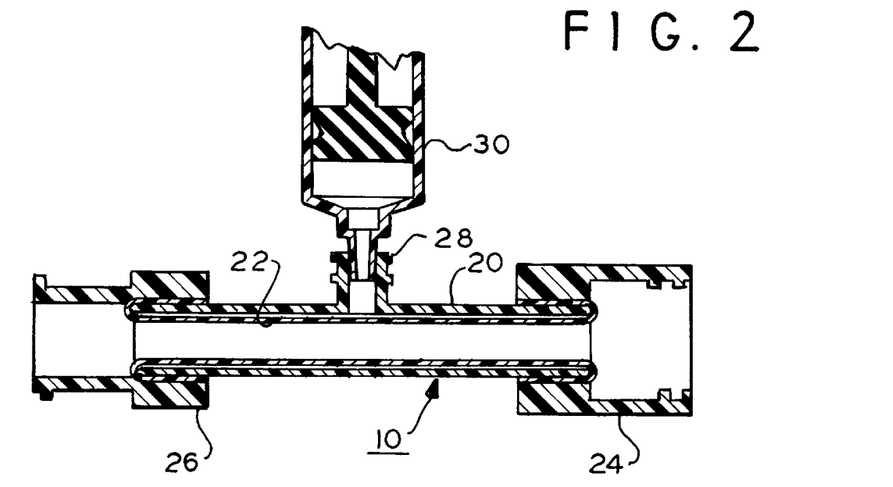
FIG. 2 is a cross sectional view of the valve of the prior art invention of FIG, 1.

Referring now to FIG. 2, the valve 10 of the foregoing prior art invention comprises an outer tubular body member 20 which is generally made of a polyurethane or other rigid or semi-rigid material that can be easily sterilized. The length of outer body 20 depends on the size of the internal diameter necessary to accommodate different size catheters for various treatment regimens. The valve body 20 can be sized so as to permit easy passage of a balloon catheter therethrough without damaging the balloon. The body 20 is lined with a flexible tubular lining 22 which is generally formed of a thin layer of high strength polyethylene or other suitable elastic material so as to completely line the interior of the valve body 20. The tubular sleeve 22 generally is longer than the body 20 and the ends are folded back about the outer ends of the body 20 and cemented about the ends of the body to form an air-tight seal about the circumference of the ends of the body 20. Suitable ferrules 24 and 26 are then sealed about the ends of the body 20 and the turned back sleeve 22 to secure the whole assembly to a form that can be easily and readily connected to other ferrules such as the ferrule 16 of the introducing sheath 12 of FIG. 1.

The provision of the inner tubular lining 22 completely sealed about both ends of the body 20 forms a compartment between the inner sleeve and outer body portion. The inner elastic sleeve 22 may be elastically deformed, as will be described in detail. The port 28 is shown as a tapered fitting for introducing of a standard hypodermic syringe for introducing air or other fluid into the compartment between the inner sleeve and outer body of the valve 10. As shown in FIG. 2, a standard hypodermic syringe 30 is provided to introduce a sterile saline solution, for instance, through the port 28 into the space between the outer body 20 and the inner sleeve 22.

Figure 3:
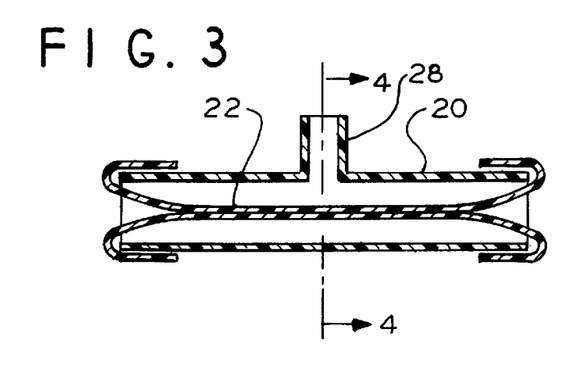
FIG. 3 is a cross sectional view of the valve of FIG. 2 in the actuated condition without a catheter present of the prior art invention of FIG. 1.
Figure 4:
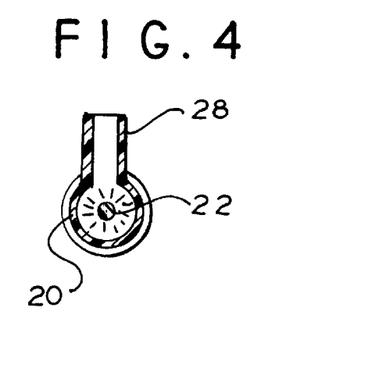
FIG. 4 is a cross sectional view taken along line 4—4 of FIG. 3 of the prior art invention of FIG. 1.

Referring now to FIG. 3, it will be seen that as air or other fluid is introduced into the space between the outer body 20 and the sleeve 22, the elastic sleeve 22 will be inwardly deformed and collapsed upon itself until it forms a solid mass at the center of the circular body 20, throughout approximately half the length of the body 20, totally closing off and sealing the valve body against fluid flow from one end to the other. The valve, as shown in FIGS. 3 and 4 is totally closed off and prohibits flow of blood or other fluids therethrough. As may be seen in FIG. 4, the center of the assembly becomes a solid mass of high strength polyethylene which, together with the remaining part of the thin tubular film, forms a complete seal at each end of the tube against any flow of fluid. If the valve 10 of FIG. 1 were actuated to the condition shown in FIG. 3, no fluid could flow through the sheath 12 in either direction.

When it is desired to permit flow of fluid through the valve 10, the hypodermic syringe 30 can be retracted to reduce the pressure and to allow the elastic sleeve 22 to return to its normal position, as shown in FIG. 2. In this configuration free flow of fluid is permitted through the valve body 20. When the tubular lining 22 has returned to its normal relaxed position of FIG. 2, a catheter having a balloon on the end thereof may be readily and easily inserted through the valve body and into the introducing sheath for insertion into the patient for the necessary treatment regimen. Alternatively, of course, the deformation of the sleeve 22 may be used to restrict but not totally shut off the flow of fluid through the valve body so that fluid flow may be regulated as well as stopped.

Figure 5:
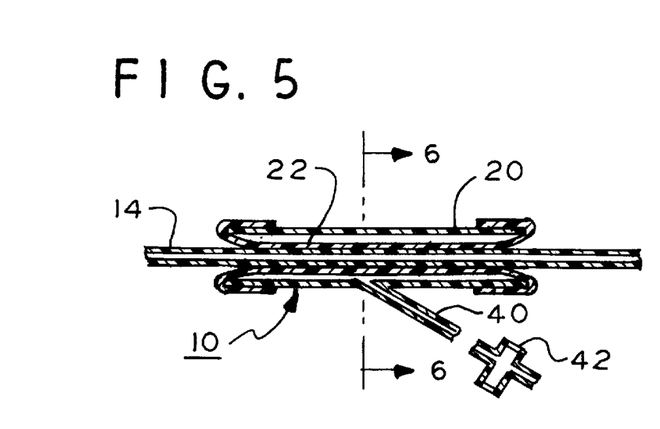
FIG. 5 is a view similar to FIG. 3 of another embodiment of the prior art invention of FIG. 1, with the valve actuated to seal around a catheter inserted therethrough.
Figure 6:
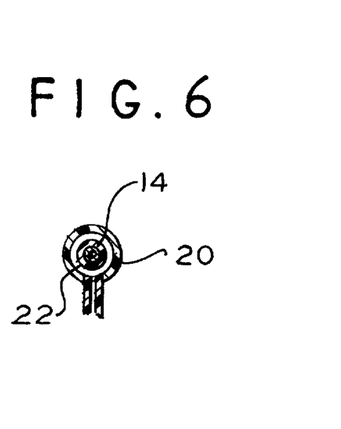
FIG. 6 is a cross sectional view taken along line 6—6 of FIG. 5 of the prior art invention of FIG. 1.

Referring now to FIG. 5, the valve 10 is shown with a catheter 14 inserted therethrough. With the valve actuated as shown in FIG. 6, a seal is formed around the circumference of the catheter to prevent any leakage of blood or other fluids past the catheter and out of the introducing sheath. By limiting the amount of pressure applied by the hypodermic syringe 30 to the tubular lining 22 of the valve 10, a sealing action may be provided around the circumference of the catheter, while still allowing it to be inserted and withdrawn from the introducing sheath, without leakage. Once the catheter is in place, if desired, the pressure applied by the hypodermic syringe may be increased sufficiently to physically hold the catheter in place by causing a sufficient length of the flexible lining 22 to grip and surround the catheter so that no other clamping mechanism is required to hold the catheter in place during use. Since the clamping pressure is applied over an extended area, there is no danger of collapsing the catheter. The catheter is thus held in place and leakage is totally sealed off thereabout during use without the necessity of a locking ferrule or other sealing device.

The flexible inner lining of the valve body 20 is generally made of a high strength polyethylene material which has a very strong non-permeable characteristic and yet can be repeatedly flexed to a very considerable degree without bursting or fatigue which might cause leakage. Wall thickness of ⅔,₀₀₀ of an inch and thinner will provide the required flexibility and strength. In a preferred embodiment of the present invention, a tubular sleeve having a wall thickness of approximately 5/10,000 of an inch has been found satisfactory. It will thus be seen that the inner sheath 22 causes virtually no restriction of the interior of the valve body 20 in the unactivated position and thus offers an easy and simple way of inserting a complicated catheter such as a balloon catheter without causing any damage to the catheter going through the valve mechanism. This high strength polyethylene tube also is extremely elastic and can be readily collapsed about the catheter to totally seal off fluid flow through the inserting sheath about the catheter and also when no catheter is present, to totally seal off the valve body itself against fluid flow. It will be recognized that the amount of sealing can be adjusted by varying the pressure or amount of fluid used to cause the deformation of the sleeve 22 into the interior of the tubular body 20. As indicated above, this fluid pressure can be increased sufficiently to physically hold a catheter in place or other wire or instrument that may be placed in the valve body so that the valve body can be used not only to prevent fluid flow, but it also can be used to clamp and position instruments relative to the valve body. By adjusting the length of the valve body and the tubular elastic sleeve relative to its diameter and the strength of any object to be clamped within it, surface pressures can be regulated so as not to collapse the catheter or other device placed within the valve 10. In at least one prior art device known to applicant, when it was attempted to clamp an outer sleeve about the inner catheter, the device actually collapsed the catheter as well as the sleeve so that the catheter could no longer be used for the introduction of medication into the patient. Applicant's valve can be adjusted to prevent leakage about an instrument wire, catheter, temperature sensor, or other apparatus inserted through the introducing sheath, as well as to completely shut off the introducing sheath against leakage of blood or other fluids.

As shown in FIG. 5, the valve body 20' may have molded as an integral part thereof a hollow tube 40 shown entering the outer body 20' at an angle of approximately 30 degree which tube has on its end a usual ferrule 42 or other mechanism for introducing the sealing and clamping fluid pressure. The body 20' can be molded with the tube 40 integral therewith for certain applications. When the valve 10, as shown in FIG. 5 is actuated about a catheter positioned therein, it will cause the flexible lining 22 to tightly wrap around and collapse upon the catheter 14 to form a seal about the outer surface of the catheter, while allowing fluid to flow through the catheter for the treatment of the patient (FIG. 6).

As shown in FIGS. 3 and 5, the extent of collapse of the flexible lining 22 onto itself or about the catheter can be varied from a very small amount to 50–75% of the length of the valve body 20 depending upon the amount of pressure applied to the cavity between the inner and outer sleeves of the body. By varying the wall thickness of the flexible sleeve 22 and the length and diameter of the body 20, various footprint pressures can be obtained for sealing about fragile or very strong catheters or other devices inserted through the valve body for a wide variety of applications of this flow control and positioning device.

THE INVENTION

The invention is premised on the observation that when a elastomeric tube is longitudinally stretched, its inner and outer cross-sectional areas decrease in direct proportion to the length to which it is stretched. The principal is more particularly depicted in FIGS. 7 and 8.

Figure 7:
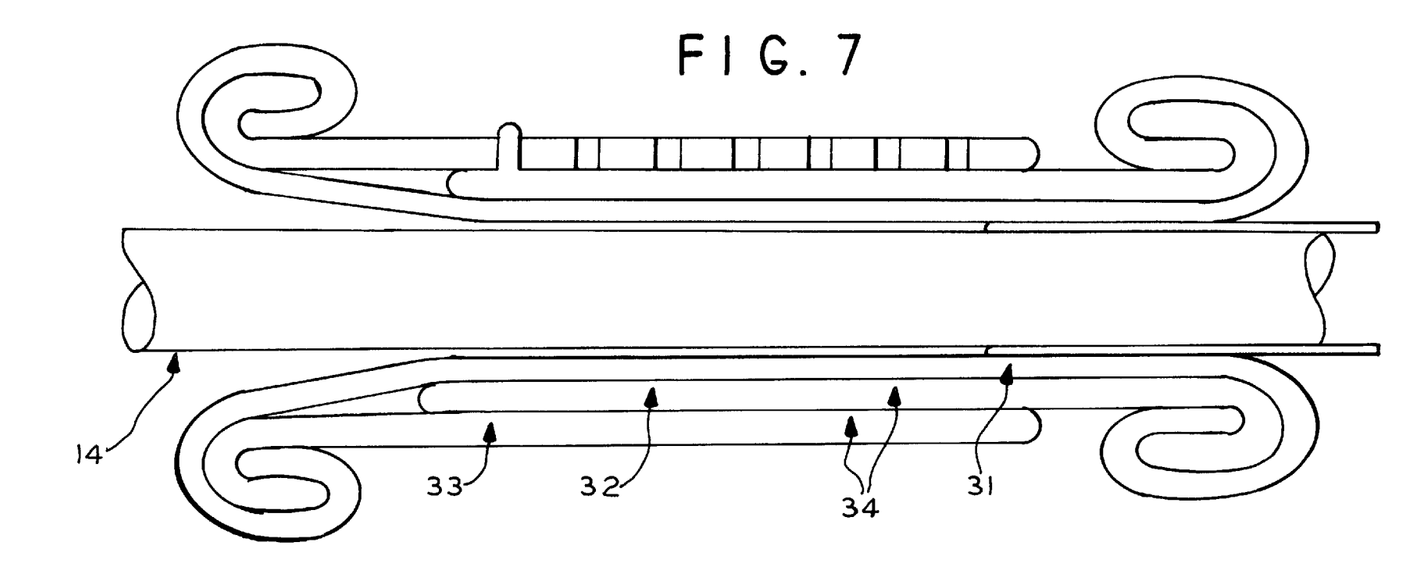
FIG. 7 shows a partial isometric view of the novel valve and catheter restraining arrangement of the instant invention.

FIG. 7 shows a cutaway partial side view of the instant invention. Depicted in FIG. 7 is the arrangement of the instant invention for selectively restricting the flow of a fluid through the annular space between an elastomeric tube (31) and a catheter (14) disposed within it, as well as selectively restricting lateral movement of the catheter (14) relative to the elastomeric tube (31). The arrangement includes a substantially rigid telescoping tube (34) for supporting the elastomeric tube (31) there within. The rigid telescoping tube (34) further includes an inner tube (32) which further includes a pin (35) disposed on the outer circumference thereof; and an outer tube (33) which further includes an opening therein forming a slot (37) (more clearly shown in FIG. 8), and a plurality of substantially equally spaced stops (36); a first clamping arrangement for fixing one end of the elastomeric tube (31) to the end of the outer tube (33) furthest from the inner tube (32); and, a second clamping arrangement for fixing the other end of the elastomeric tube (31) to the end of the inner tube (32) farthest from the outer tube (33);

The inner diameter of the elastomeric tube (31) is decreased in direct proportion to the length of the substantially rigid telescoping tube (34) as it is stretched and thereby increased by causing the pin (35) to be placed in each one of the substantially equally spaced stops (36) progressively closer to the end of the outer tube (33) furthest from the inner tube (32). Similarly, the inner diameter of the elastomeric tube is increased in direct proportion to the length of the substantially rigid telescoping tube (34) as it is relaxed and decreased by causing the pin (35) to be placed in each one of the substantially equally spaced stops (36) progressively farther from the end of the outer tube (33) furthest from the inner tube.

Figure 8:
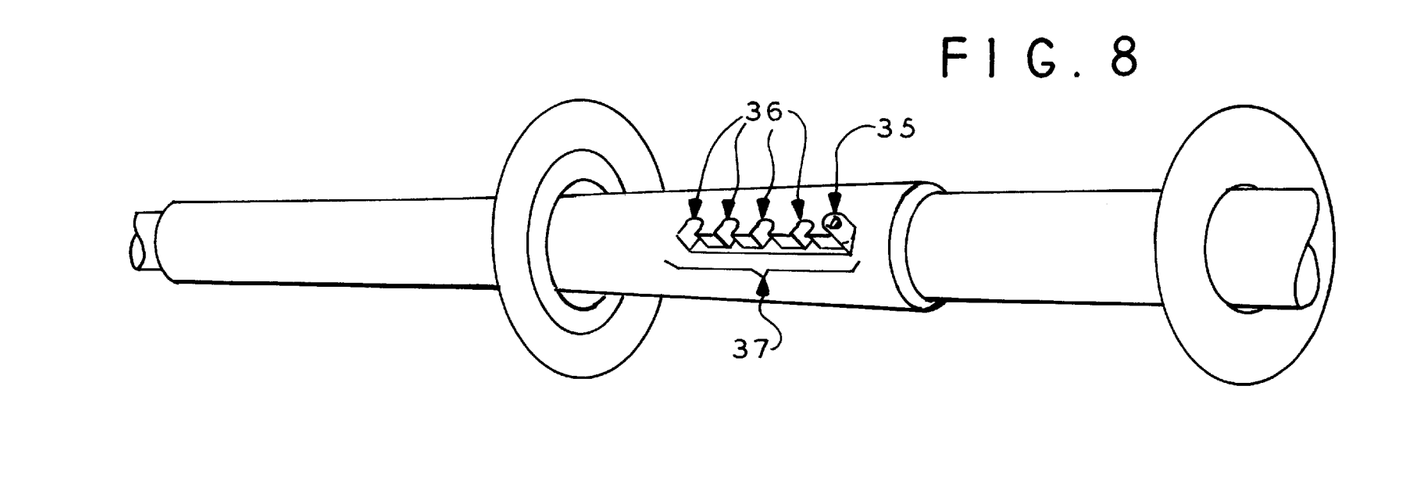
FIG. 8 shows a partial side sectional view of the novel valve and catheter restraining arrangement of the instant invention as shown in FIG. 7.

FIG. 8 shows a partial isometric view of the novel arrangement of the invention. The relationship between slot (37), stops (36) and pin (35) are depicted with particularity.

The elastomeric tube (31) can be constructed of substantially any known elastomer suitable for medical applications. An elastomer as contemplated by the instant invention, is any member of a class of synthetic polymeric substances (giant molecules consisting of linked smaller molecules or monomers) possessing rubberlike qualities, especially the ability to regain shape after deformation; toughness; and resistance to weathering and chemical attack.

More specifically such elastomers typically comprise a family of plastic known as copolymers. A copolymer, as contemplated by the instant invention is any of a diverse class of substances of high molecular weight prepared by chemical combination, usually into long chains, of molecules of two or more simple compounds (the monomers forming the polymer). The structural units derived from the different monomers may be present in regular alternation or in random order, or strings of several units of one kind may alternate with strings of another. Elastomers used for medical purposes are commonly called biomaterials. The majority of biomaterials used in humans are synthetic polymers such as the polyurethanes or Dacron (trademark; chemical name polyethylene terephthalate), rather than polymers of biological origin such as proteins or polysaccharides. The common synthetic biomaterials and their applications. Their properties vary widely, from the soft and delicate water-absorbing hydrogels made into contact lenses to the resilient elastomers found in short- and long-term cardiovascular devices or the high-strength acrylics used in orthopedics and dentistry. The properties of any material are governed by its chemical composition and by the intra- and intermolecular forces that dictate its molecular organization. Macromolecular structure in turn affects macroscopic properties and, ultimately, the interfacial behavior of the material in contact with blood or host tissues.

Preferred elastomers of the invention are natural and synthetic rubbers. Synthetic Rubber are any artificially produced substance that resembles natural rubber in essential chemical and physical properties can be called synthetic rubber. Such substances are produced by chemical reactions, known as condensation or polymerization, of certain unsaturated hydrocarbons. The basic units of synthetic rubber are monomers, which are compounds of relatively low molecular weight that form the building units of huge molecules called polymers. After fabrication, the synthetic rubber is cured by vulcanization.

The origin of synthetic-rubber technology can be traced to 1860, when the British chemist Charles Hanson Greville Williams determined that natural rubber was a polymer of the monomer isoprene, which has the chemical formula $CH_2{:}C(CH_3)CH{:}CH_2$. Many efforts were made during the next 70 years to synthesize rubber in the laboratory by using isoprene as the monomer. Other monomers also were investigated, and during World War I (1914–1918) German chemists polymerized dimethylbutadiene (formula $CH_2{:}C(CH_3)C(CH_3){:}CH_2$) producing a synthetic rubber called methyl rubber, which was of limited usefulness.

A breakthrough in synthetic-rubber research did not occur, however, until about 1930, when the American chemist Wallace Hume Carothers and the German scientist Hermann Staudinger did scientific work that contributed greatly to present-day knowledge that polymers are huge, chainlike molecules made of large numbers of monomers, and that synthetic rubber can be prepared from monomers other than isoprene.

Synthetic-rubber research initiated in the United States during World War II led to the synthesis of a polymer of isoprene identical in chemical composition with natural rubber. One of the first successful synthetic rubbers resulting from Carothers's research was neoprene, which is the polymer of the monomer chloroprene, chemical formula $CH_2{:}C(Cl)CH{:}CH_2$. The raw materials of chloroprene are acetylene and hydrochloric acid. Developed in 1931, neoprene has high resistance to heat and such chemicals as oils and gasoline. Neoprene is used in hose for conveying gasoline and as an insulating material for cables and in machinery. In 1935 German chemists developed the first of a group of synthetic rubbers called Buna, which is produced by copolymerization—that is, the polymerization of two monomers, called comonomers. The name Buna is derived from the initial letters of butadiene, used as one of the comonomers, and natrium (sodium), which was used as a catalyst. One of these products, Buna-N, uses acrylonitrile ($CH_2{:}CH(CN)$) as the other comonomer. Acrylonitrile is produced from cyanide. Buna-N is valuable for uses requiring resistance to the action of oils or abrasion. During World War II a Buna-type rubber called GR-S (Government Rubber-Styrene) was designated as the general-purpose rubber for the U.S. war effort. The basic rubber produced by the present-day U.S. synthetic-rubber industry, GR-S is a copolymer of butadiene and styrene. The various grades of GR-S are classified in two categories, regular and cold, depending on the temperatures of copolymerization. Cold GR-S types, which exhibit superior properties, are prepared at 5° C. (41° F.); regular GR-S types are prepared at temperatures of 50° C. (122° F.). Cold GR-S is used to make longer-wearing tires for automobiles and trucks. Butyl rubber, produced initially in 1940, is prepared by copolymerization of isobutylene with butadiene or isoprene. It is plastic and can be compounded like natural rubber, but is difficult to vulcanize. Athough butyl rubber is not as resilient as natural rubber and other synthetics, it is extremely resistant to oxidation and the action of corrosive chemicals. Because of its low permeability to gas, butyl rubber is used widely for inner tubes in automobile tires. Many other types of synthetic rubber have been developed for purposes requiring specific properties. One such specialty rubber, called Koroseal, is a polymer of vinyl chloride ($CH_2{:}CHCl$). Vmyl chloride polymers are heat-, electricity-, and corrosion-resistant and are unaffected by exposure to light or by long storage. Koroseal cannot be vulcanized, but, when not subjected to high temperatures, it is more resistant to abrasion than natural rubber or leather.

Another specialty rubber is Thiokol, produced by copolymerization of ethylene dichloride (CHCl:CHCl), and sodium tetrasulfide ($Na_2S_4$). This type, which can be compounded and vulcanized like natural rubber, is resistant to the action of oils and to organic solvents used for lacquers, and is useful for electrical insulation because it does not deteriorate when exposed to electrical discharge and light.

Many other types of synthetic rubber are produced in the United States, mostly by methods similar to those described above. Certain changes in the process or the polymerization recipes have succeeded in improving quality as well as reducing production costs. In one outstanding development, petroleum oil was used as an additive; it lowered the cost by conserving a substantial amount of synthetic-rubber stock. Tires made from such oil-extended rubber are very durable. Other important advances include the development of synthetic foam rubber, used mainly for upholstery, mattresses, and pillows; and cellular-crepe rubber, used by the shoe industry. The rigid components of the instant invention can also be constructed of medically suitable plastics, such as thermosets or thermosetting polymers and thermoplastics.

Plastics which are more preferred as a material of construction for the rigid components of the invention are thermoplastics. Many common thermoplastics, such as polyethylene and polyester, are used as biomaterials. Thermoplastics usually exhibit moderate to high tensile strength (5 to 1,000 megapascals) with moderate elongation (2 to 100 percent), and they undergo plastic deformation at high strains. Thermoplastics consist of linear or branched polymer chains; consequently, most can undergo reversible melt-solid transformation on heating, which allows for relatively easy processing or reprocessing. Depending on the structure and molecular organization of the polymer chains, thermoplastics may be amorphous (e.g., polystyrene), semicrystalline (e.g., low-density polyethylene), or highly crystalline (e.g., high-density polyethylene), or they may be processed into highly crystalline textile fibres (e.g., polyester Dacron).

Thermosets or thermosetting polymers constitute a species of biomaterials which find only limited application in medicine, but their characteristic properties, which combine high strength and chemical resistance, are useful for some orthopedic and dental devices. Thermosetting polymers such as epoxies and acrylics are chemically inert, and they also have high modulus and tensile properties with negligible elongation (1 to 2 percent). The polymer chains in these materials are highly cross-linked and therefore have severely restricted macromolecular mobility; this limits extension of the polymer chains under an applied load. As a result, thermosets are strong but brittle materials. Thus, they are less preferred for purposes of the instant invention.

The valve of the present invention can be used in a wide variety of applications as well as a shut off valve for preventing leakage of blood or other fluids from an inserting sheath. It can be used to temporarily shut off the flow of blood in bypass vein or artery applications; it can also be used to position instruments in a catheter or other tubular inserting sheath; and it can also be used to prevent leakage around fragile or delicate catheters as well as providing sealing around specialized catheters having balloons or other devices on the end thereof. In the later application, the sleeve is totally unpressurized to allow free passage of the tip of the catheter carrying the specialized instrumentation and then it is suitably inflated to collapse about and seal off leakage of fluids about the catheter during the rest of its insertion into proper operating position and during its use and withdrawal.

A unique fluid controlling device having a wide variety of applications has thus been provided for effectively controlling the flow of fluids through a conduit and for positioning a device within a conduit while simultaneously preventing leakage around the device within the conduit. While this invention has been explained with reference to the structure disclosed herein, it is not confined to the details as set forth and this application is intended to cover any modifications and changes as may come within the scope of the following claims.

I claim:

1. A combination sealing/positioning device for use on an introducer sheath for a balloon dilation catheter in which leakage during insertion and withdrawal is eliminated and a selected position maintained which comprises:

a substantially rigid telescoping tube having an elastomeric tube therewithin, which includes an arrangement for variably fixing said substantially rigid telescoping tube to a desired length and a catheter sheath disposed in one end thereof, a first clamping arrangement for fixing one end of said elastomeric tube to one of said substantially rigid telescoping tube; and, a second clamping arrangement for fixing the other end of said elastomeric tube to the other end of said substantially rigid telescoping tube;

wherein said catheter is disposed within said elastomeric tube; and said elastomeric tube is disposed within said substantially rigid telescoping tube; and, whereby the inner diameter of said elastomeric tube is selectively varied in direct proportion to said desired length of said substantially rigid telescoping tube so that a balloon dilation catheter can be introduced through said elastomeric tube into said catheter sheath without damage to the balloon and fluid flow can be sealed off while said catheter is being installed or withdrawn through said catheter sheath.

2. A sealing/positioning device according to claim 1 wherein said device is sized, dimensioned and designed and the materials of construction thereof are selected to apply to a dilation catheter mounted therein an area of contact sufficient to seal off fluid flow thereabout upon introducing a first amount of fluid into said fluid receiving chamber; and to hold said dilation catheter fixed in position upon introducing a second amount of fluid into said fluid receiving chamber without damaging said dilation catheter.

3. The arrangement of claim 1 wherein said elastomeric tube is constructed from a material selected from the group consisting of natural rubber, synthetic rubber and combinations thereof.

4. An arrangement for selectively restricting the flow of a fluid through the anular space between an elastomeric tube and a substantially rigid tube disposed within it and for selectively restricting lateral movement if said substantially rigid tube relative to said elastomeric tube, comprising:

a substantially rigid telescoping tube for supporting said elastomeric tube therewithin, which includes an inner tube further including a pin disposed on the outer circumference thereof and an outer tube further including an opening therein forming a slot and a plurality of substantially equally spaced stops; a first clamping arrangement for fixing one end of said elastomeric tube to the end of said outer tube furthest from said inner tube; and, a second clamping arrangement for fixing the other end of said elastomeric tube to the end of said inner tube furthest from said outer tube;

wherein said substantially rigid tube is disposed with said elastomeric tube; and said elasotomeric tube is disposed within said substantially rigid telescoping tube; and, whereby the inner diameter of said elastomeric tube is decreased in direct proportion to the length of said substantially rigid telescoping tube as it is increased by causing said pin to be placed in each one of said substantially equally spaced stops progressively closer to said end of said outer tube furthest from said inner tube; and, the inner diameter of said elastomeric tube is increased in direct proportion to the length of said substantially rigid telescoping tube as it is decrease by causing said pin to be placed in each one of said substantially equally spaced stops progressively farther from said end of said outer tube furthest from said inner tube.

5. The arrangement of claim 4 wherein said elastomeric tube is constructed from a material selected from the group consisting of natural rubber, synthetic rubber and combinations thereof.

6. An arrangement for selectively restricting the flow of a fluid through the anular space between an elastomeric tube and a substantially rigid tube disposed within it and for selectively restricting lateral movement if said substantially rigid tube relative to said elastomeric tube, comprising:

a substantially rigid telescoping tube for supporting said elastomeric tube therewithin, which includes an arrangement for variably fixing said substantially rigid telescoping tube to a desired length; a first clamping arrangement for fixing one end of said elastomeric tube to one of said substantially rigid telescoping tube; and, a second clamping arrangement for fixing the other end of said elastomeric tube to the other end of said substantially rigid telescoping tube;

wherein said substantially rigid tube is disposed with said elastomeric tube; and said elasotomeric tube is disposed within said substantially rigid telescoping tube; and, whereby the inner diameter of said elastomeric tube is selectively varied in direct proportion to said desired length of said substantially rigid telescoping tube.

7. The arrangement of claim 6 wherein said elastomeric tube is constructed from a material selected from the group consisting of natural rubber, synthetic rubber and combinations thereof.

* * * * *